United States Patent [19]

Grollier et al.

[11] Patent Number: 5,194,260
[45] Date of Patent: Mar. 16, 1993

[54] COSMETIC COMPOSITION FOR THE HAIR CONTAINS A FILM FORMING POLYMER AND A SILICONE INCORPORATED IN A WAX MICRODISPERSION AND A COSMETIC TREATMENT USING THE SAME

[75] Inventors: Jean-François Grollier; Isabelle Rellet, both of Paris; Lyonel Peritz, Saint-Cloud, all of France

[73] Assignee: L'Oreal, Paris, France

[21] Appl. No.: 748,650

[22] Filed: Aug. 22, 1991

[30] Foreign Application Priority Data

Aug. 23, 1990 [FR] France .................. 90 10602

[51] Int. Cl.$^5$ ................................. A61K 7/11
[52] U.S. Cl. ......................... 424/401; 424/71; 424/DIG. 2
[58] Field of Search ................. 424/71, DIG. 2, 401

[56] References Cited

U.S. PATENT DOCUMENTS

| | | | |
|---|---|---|---|
| Re. 29,871 | 12/1978 | Papantoniou et al. | 424/70 |
| 4,336,246 | 6/1982 | Leon-Pekarek | 424/DIG. 2 |
| 4,551,330 | 11/1985 | Wagman | 424/59 |
| 4,839,167 | 6/1989 | Yamamoto et al. | 424/DIG. 2 |
| 5,039,519 | 8/1991 | Inoue et al. | 424/71 |

FOREIGN PATENT DOCUMENTS 374332  6/1990  European Pat. Off. .

*Primary Examiner*—Thurman K. Page
*Assistant Examiner*—Amy Hulina
*Attorney, Agent, or Firm*—Cushman, Darby & Cushman

[57] ABSTRACT

A cosmetic composition for the hair contains at least one film forming polymer and at least one silicone incorporated into a support consisting essentially of a wax microdispersion in an aqueous liquid vehicle. The dispersed phase of this vehicle is a stable microdispersion of particles having a size lower than 500 nm. The particles consist essentially of a wax or mixture of waxes having a final melting point greater than 60° C. and lower than 100° C. which is capable of forming a microdispersion as defined above. The composition contains from 0.1 to 40 weight percent of wax and a sufficient amount of at least one emulsifying agent. A process for the cosmetic treatment of the hair involves applying the above-defined composition to the hair.

13 Claims, No Drawings

COSMETIC COMPOSITION FOR THE HAIR CONTAINS A FILM FORMING POLYMER AND A SILICONE INCORPORATED IN A WAX MICRODISPERSION AND A COSMETIC TREATMENT USING THE SAME

The present invention relates to a cosmetic composition for hair containing a film forming polymer and a silicone incorporated in a wax microdispersion, as well as to a cosmetic treatment process for the hair using such a composition.

It is known that numerous capillary cosmetic compositions contain a film forming polymer which, when applied in the form of a solution, permits the formation, after evaporation of the solvent, a film sheathing the hair. It is known that the film forming polymers employed in the cosmetic compositions for the hair have in common principally the property of reinforcing the hold of the hair style.

It is also known to incorporate in cosmetic compositions for the hair silicones which exhibit principally the property of improving the softness of the hair.

It is also known that it is possible to obtain microemulsions with certain oils and stable and limitlessly water dilutable microdispersions with certain waxes, without aggregation or sedimentation of the particles in suspension. Wax microdispersions are obtained by melting the wax in the presence of an anionic or nonionic surfactant, and optionally a portion of water, then progressively adding hot water with stirring. The intermediate formation of a water-in-oil type emulsion is observed followed by a phase inversion with the final obtention of an oil-in-water type emulsion. On cooling, a stable microdispersion of solid colloidal wax particles is obtained; see for example, "Microemulsions Theory and Practice", L. M. Prince Ed. Academic Press, (1977) pages 21-32.

Until now these wax microdispersions were employed principally to shine leather articles and plastic material ground coverings.

In European patent application No. 90 400515, filed Feb. 23, 1990 and entitled "Utilization as cosmetic composition for hair, of a wax microdispersion, and process of treating hair with such a composition", there has been described the use of, as a cosmetic composition or support for a cosmetic composition for the hair, a fluid composition consisting essentially of a stable wax microdispersion in an aqueous liquid vehicle.

It has now been discovered that, in a surprising manner, cosmetic compositions for the hair containing a film forming polymer and a silicone in a wax microdispersion impart good properties of softness to the hair and hair style hold, whereas compositions containing only the wax microdispersion and a silicone lessen the hold of the hair style and that compositions containing only the wax microdispersion and film forming polymer lessen the softness of the hair.

The present invention thus relates to a cosmetic composition for the hair comprising at least one film forming polymer and at least one silicone incorporated into a support consisting essentially of a wax dispersion in an aqueous liquid vehicle of which the dispersed phase is a stable microdispersion of particles having a size lower then 50 nm, the said particles consisting essentially of a wax or mixture of waxes, the said wax or mixture of waxes having a final melting point greater than 60° C. and lower than 100° C. and being capable of forming a microdispersion such as defined above, the said composition containing, by weight, from 0.1 to 40 percent of wax and a sufficient amount of at least one emulsifying agent.

It is known that waxes are natural substances (animal or vegetable) or synthetic substances, solid at ordinary temperature (21° C.), having generally a certain plasticity, which are insoluble in water, soluble in oils, and which are capable of forming water repellent films. Concerning the definition of waxes and their uses in cosmetology, reference can be made, for example, to P. D. Dorgan, Drug and Cosmetic Industry, December 1983, pages 30-33, and Handbook for Cosmetic Science, H. W. Hibbot ed., Pergamon Press, Oxford (1963), page 60.

The wax or mixture of waxes employed in the composition according to the present invention must be capable of giving, in combination with emulsifying agents, principally nonionic and/or anionic emulsifying agents, in accordance with the process described above, stable microdispersions having particle sizes lower than 500 nm. The useful waxes or mixture of waxes can be selected by simple routine experimentation.

The wax is principally a wax selected from Carnauba wax, Candelilla wax, Alfa wax and their mixtures; the wax can contain, other than the waxes already mentioned, another wax or a mixture of other waxes, for example, a paraffin wax; the weight amount of Carnauba wax and/or Candelilla wax and/or Alfa wax, in such mixtures, is preferably greater than or equal to 50 percent.

The vegetable waxes of Carnauba (extract of Copernicia Cerifera), of Candelilla (extract of Euphorbies Cerifera and of Pedilantus Pavonis), and of Alfa (extract of Stipa Tenacissima) are commercial products.

It is also possible, in accordance with the present invention, to employ ceramides, principally in combination with at least one of the waxes mentioned above.

The ceramides are the principal lipids constituted by the intercorenocytal spaces of the corneum stratum. They have been described, in particular, by Downing in Science, 1982, pages 1261-2, Vol. 18. The ceramides have already been employed principally in cosmetic compositions for the hair: see for example European patent application 0278505.

These ceramides are generally difficult to disperse in cosmetic compositions. In the compositions of the present invention, it is possible to disperse them easily.

The amount of waxes, in the composition, is for example from 0.1 to 20 percent, principally from 1 to 15 percent, and in particular from 1 to 10 percent.

The weight amount of wax in the particles of the microdisperison is generally greater than 90 percent relative to the weight of the particles, and is most often greater than 95 percent, the remainder being constituted by liposoluble ingredients optionally present (not including the emulsifying agents).

The weight ratio wax/emulsifying agent can vary in the range of 1 to 20, principally 2 to 10.

It is also possible to prepare wax microdispersions by using commercial mixtures of self-emulsifying waxes containing the wax and the emulsifying agents. There can be employed, for example, the wax sold under the trade name "CIRE AUTO LUSTRANTE OFR" by Tiscco, Bobigny, France, which contains Carnauba wax and paraffin wax, in combination with nonionic emulsifying agents, or the self-emulsifying wax sold under the trade name "CERAX A. O. 28/B" by La Ceresine, Marseille, France, which contains Alfa wax in combination with a nonionic emulsifying agent. These commercial mixtures permit to prepare wax microdispersion by addition of water in accordance with the process described above.

The emulsifying agent employed to permit the preparation of stable wax microdisperison, such as defined above, is preferably an anionic or nonionic surfactant. The concentration of the emulsifying agent is at least equal to the concentration necessary to obtain such a microdispersion. This minimum concentration can be determined in each case by simple routine experimentation. Generally, it can vary from 0.01 to 25 percent by weight, relative to the total weight of the composition, and in particular from 0.1 to 10 percent by weight.

The anionic surfactants employed have preferably a lipophile-hydrophile balance (HLB) ranging from 10 to 40. They are principally salts of fatty acids (for example, alkaline salts or organic salts such as amine salts), the said fatty acids having for example from 12 to 18 carbon atoms and being able to have a double bond as in the case of oleic acid; the alkaline salts or salts of organic bases with alkyl-sulfuric acids and alkyl-sulfonic acids having 12 to 18 carbon atoms, alkyl-arylsulfonic acids of which the alkyl chain contains 6 to 16 carbon atoms, the aryl group being for example a phenyl group. These are also ether-sulfates, in particular, the sulfating products of fatty alcohols and polyalkoxylated alkylphenols in which the aliphatic chain contains 6 to 20 carbon atoms and the polyalkoxylated chain has 1–30 oxyalkylene units, in particular, oxyethylene, oxypropylene or oxybutylene.

All these anionic surfactants are well known and many among them are commercial products.

The nonionic surfactants are principally polyalkoxylated and/or polyglycerolated surfactants. They are principally polyalkoxylated and/or polyglycerolated fatty acids or amides of fatty acids; esters of fatty acids and polyalkoxylated and/or polyglycerolated polyols; fatty alcohols or polyalkoxylated and/or polyglycerolated alkylphenols; 1,2- or 1,3-alkanediols or alkenediols, polyalkoxylated and/or polyglycerolated; alkylethers of 1,2- or 1,3-alkanediols or alkenediols polyalkoxylated and/or polyglycerolated. The fatty acids or alcohols, optionally unsaturated, have for example 12 to 24 carbon atoms. The alkyl chain of the alkylphenols has for example 6 to 16 carbon atoms. The alkanediols and alkenediols have from 9 to 24 carbon atoms. The alkyl of the alkyethers has from 4 to 20 carbon atoms and the number of oxyalkylene units or ($CH_2CHOHCH_2O$) units can range from 2 to 40.

The polyalkoxylated nonionic derivatives are principally polyoxyethylenated derivatives optionally polyoxypropylenated.

The polyalkoxylated fatty acids are commercial products, principally products sold under the name "MYRJ" by Atlas.

The esters of fatty acids and polyoxyethylenated polyols for which the polyol is sorbitol are known products (Polysorbate and products sold under the name "TWEEN" by Atlas).

The polyoxyethylenated fatty alcohols are commercial products, principally those sold under the name "BRIJ" by Atlas.

The polyglycerolated fatty alcohols, the polyglycerolated alkanediols or alkenediols, or the alkylethers of polyglycerolated alkanediols or alkenediols can be prepared, for example, in accordance with the processes described in French patents 1.477.048, 2.025.681, 2.091.516 and 2.465.780, or in accordance with analogous processes.

The polyglycerolated fatty acids or amides of fatty acids are principally described in French patent 1.484.723 or again are commercial products such as those sold under the name "PLUROL" by Gattefosse or "DREWPOL" by the Stefan Company.

As indicated above, the continuous phase of the microdispersion is an aqueous phase. Generally the composition of the present invention contains, by weight, at least 35 percent water. The amount of water in the liquid phase generally varies from 80 to 100 percent relative to the weight of the liquid phase.

The silicones present in the composition of the invention are polyorganosiloxanes. It is a question of known products which can be provided in the form of oils, gums, resins or waxes. In these three latter cases, they can be added to the composition in the form of a solution in an organic solvent, or in admixture with liquid silicones in which they are soluble.

In a general fashion, the silicones are polymers containing units of raw formula I:

$$[R_n SiO_{\frac{4-n}{2}}] \qquad (I)$$

These polymers contain repeating units which are the units of formula (I) for which $n=2$. The R substituents present in these repeating units are organic groups. The R groups linked to the same silicon atom can be identical or different. Besides the same polymer molecule can contain different repeating units.

The repeating units corresponding to $n=2$ impart to the polymer molecule a linear or cyclic structure of which the chain is constituted by siloxane bonds. In the case of a linear polymer, units corresponding to $n=3$ constitute terminal groups.

Besides, the polyorganosiloxanes can contain crosslinking units interposed between repeating units. These crosslinking units corresponds to formula (I) with $n=1$ or $n=0$.

In the repeating units ($n=2$) and crosslinking units corresponding to $n=1$, the R groups can represent principally alkyl, cycloalkyl or aryl groups and can carry besides, functional groups (ethers, amines, carboxyls, hydroxyls, thiols, esters, sulfonates, sulfates, etc.). The alkyl groups have for example 1–20 carbon atoms; the cycloalkyl groups have for example 5 or 6 chains; the aryl groups are principally phenyl groups.

In the case of terminal groups corresponding to $n=3$, one of the R groups attached to the terminal silicon can, moreover, represent another group such as an OH group.

The silicones which respond to the definition given above are known compounds.

The weight amount of silicones can generally vary from 0.01 to 1 percent and preferably from 0.02 to 0.5 percent by weight, based on the total weight of the composition.

There are now described, in more detail below, various classes of silicones which can be employed in the composition of the present invention.

The silicones used, in accordance with the present invention, are polyorganosiloxanes which can be provided in the form of oils, gums or resins.

The more particularly employed polyorganosiloxanes, in accordance with the invention, are selected from volatile silicones which have a boiling point generally between 60° and 260° C., or even non-volatile silicones selected in particular from polyalkylsiloxanes, polyarylsiloxanes, polyalkylarylsiloxanes, polyethersiloxane copolymers organomodified or not or silicone gums and resins, polysiloxanes modified by organofunctional groups as well as their mixtures.

They are more particularly selected from among the polyalkylsiloxanes, among which there can be mentioned principally linear polydimethylsiloxanes having trimethylsilyl terminal groups, having a viscosity of $5 \times 10^{-6}$ to 2.5 m$^2$/s at 25° C. and preferably $1 \times 10^{-5}$ to 1 m$^2$/s.

Among these polyalkylsiloxanes there can be mentioned, as nonlimiting, the following commercial products:

series 47 and 70 047 "SILBIONE" oils sold by Rhone Poulenc, such as for example "47 V 500.000" oil;

series 200 oils of Dow Corning;

the "VISCASIL" oils of General Electric and certain oils of the SF series (SF96, SF18) of General Electric.

Mention can also be made of the linear polydimethylsiloxanes having terminal dimethylsilanol groups such as the oils of the 48 series of Rhone Poulenc.

In this class of polyalkylsiloxanes, mention can also be made of the products sold under the trade names "ABIL WAX 9800" and "ABIL WAX 9801" by Goldschmidt which are polyalkyl ($C_1$-$C_{20}$) siloxanes.

Among the polyalkylarylsiloxanes mention can be made of the polydimethylmethylphenylsiloxanes, linear and/or branched polydimethyldiphenylsiloxanes having a viscosity of $1 \times 10^{-5}$ to $5 \times 10^{-2}$ m$^2$/s at 25° C.

Among these polyalkylarylsiloxanes, mention can be made, for example, and without limitation, of the following commercial products:

the 70641 series "SILBIONE" oils of Rhone Poulenc, the 70633 and 763 series "RHODORSIL" oils of Rhone Poulenc, the "DC 566 Cosmetic Grad Fluid" oil of Dow Corning, the "PK" series silicones of Bayer, such as "PK 20", the PN and PH series of silicones by Bayer such as the products, "PN 1000" and PH 1000", and certain SF series of oils of General Electric such as "SF 1023", "SF 1154", "SF 1250" and "SF 1265".

The useful silicone gums, in accordance with the present invention, are polydiorganosiloxanes having high molecular masses, between 200,000 and 1,000,000, employed alone or in admixture with a solvent. This solvent can be selected from volatile silicones, polydimethylsiloxane oils (PDMS), polyphenylmethylsiloxane oils (PPMS), isoparaffins, the chloride of methylene, pentane, dodecane, tridecane, tetradecane or their mixtures.

There can be more particularly mentioned the following products:

polydimethylsiloxane/methylvinylsiloxane gum,
polydiemthylsiloxane/diphenylsiloxane gum,
polydimethylsiloxane/phenylmethylsiloxane gum and
polydimethylsiloxane/diphenylsiloxane/methylvinylsiloxane gum.

The more particularly useful products are mixtures such as:

mixtures formed starting with a polydimethylsiloxane hydroxylated at the end of the chain (called dimethiconol according to the nomenclature in the CTFA dictionary) and a cyclic polydimethylsiloxane (called cyclomethicone according to the nomenclature in the CTFA dictionary), such as the product "Q2 1401" sold by Dow Corning, mixture formed starting with a polydimethylsiloxane gum with a cyclic silicone, such as the product "SF 1214 Silicone Fluid" of General Electric (which is an "SE 30" gum, corresponding to a dimethicone, having a molecular weight of 500,000 dissolved in "SF 1202 Silicone Fluid" corresponding to decamethylcyclopentasiloxane, and mixtures of two PDMS of different viscosities, principally of a PDMS gum and a PDMS oil, such as the product "SF 1236" of General Electric. The product "SF 1236" is a mixture of an "SE 30" gum defined above having a viscosity of 20 m$^2$/s and an "SF 96" oil having a viscosity of $5 \times 10^{-6}$ m$^2$/s (15% of "SE 30" gum and 85% of "SF 96" oil).

The organopolysiloxane resins, in accordance with the present invention, are crosslinked siloxanic systems including $R_2SiO_{2/2}$, $RSiO_{3/2}$ and $SiO_{4/2}$ units. Among these compounds, the more particularly preferred products are those in which R represents a lower alkyl or phenyl.

Among these resins mention can be made of the product sold under the trade name "DOW CORNING 593" or those sold under the trade names "Silicones Fluid 4230" and SS 4267" by General Electric and which are of the dimethyl/trimethyl siloxane type.

The organomodified silicones are silicones defined above and having in their structure one or more organofunctional groups directly fixed on the siloxanic chain or fixed by the intermediate of a hydrocarbon radical.

Among these silicones mention can be made of, for example, silicones carrying:

1. polyethyleneoxy and/or polypropyleneoxy groups optionally carrying alkyl groups such as:

the product called dimethicone copolyol, sold by Dow Corning under the name "DC 1248" and the $C_{12}$ alkyl methicone copolyol sold by Dow Corning under the name "Q2 5200", the "SILWIT L722, L7500, L77, AND L711" oils sold by Union Carbide.

2. amine groups, substituted or not, such as the products sold under the names "GP4 Silicone Fluid" and "GP 7100" by Genesee or the products sold under the name "Q2 8220" and "DC 929" by Dow Corning. The substituted amine groups are in particular, ($C_1$-$C_4$) aminoalkyl groups.

3. thiol groups such as in the "GP 72A" and GP 71" products of Genesee.

4. carboxylate groups such as in the products described in EP 186507 of the Chisso corporation.

5. alkoxylated groups such as the product sold under the trade name "Silicone copolymer F-755" by SWS Silicones, and "ABIL WAX 2428, 2434 and 2440" by Goldschmidt.

6. hydroxylated groups, as the polyorganosiloxanes having a hydroxylalkyl function, described in French patent application No. FR 85 16334, having the following formula (II):

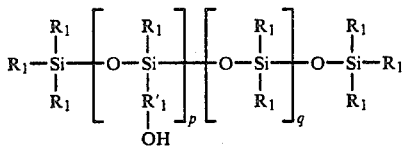
(II)

wherein the $R_1$ radicals, each independently, are selected from methyl and phenyl, at least 60 mole percent of the $R_1$ radicals representing methyl, the $R'_1$ radical is a divalent $C_2$-$C_{18}$ alkylene, p ranges from 1 to 30 inclusive, and q ranges from 1 to 150 inclusive. 7. acyloxylalkyl groups such as for example the polyorganosiloxanes described in French patent No. FR 88 17433, having the following formula (III):

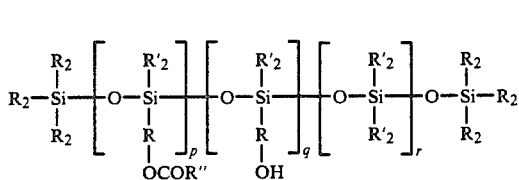
(III)

wherein $R_2$ represents methyl, phenyl, —OCOR", hydroxyl, only one of the $R_2$ radicals by a silicon atom can be OH, $R'_2$ represents methyl or phenyl, with at least 60 mole percent of all of the $R_2$ and $R'_2$ radicals representing methyl, R" represents a $C_8$-$C_{20}$ alkyl or alkenyl, R represents a linear or branched $C_2$-$C_{18}$ divalent alkylene, r ranges from 1 to 120 inclusive, p ranges from 1 to 30, q is equal to 0 or is lower than 0.5 p, p+q ranges from 1 to 30. The polyorganosiloxanes of formula (III) can contain

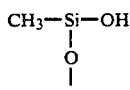

groups in amounts not exceeding 15% of the sum p+q+r.

The compounds of formula (III) can be prepared by esterification of polyorganosiloxanes having a hydroxyalkyl function of formula (II) above. The esterification is carried out in a known manner with an acid R"COOH or an acid anhydride, at a temperature between 100° and 250° C. in the optional presence of a catalyst such as aluminum chloride or zinc chloride or a strong acid such as hydrochloric acid or sulfuric acid.

A transesterification can also be effected by heating at 100°-150° C. a methyl ester of the formula R"COOCH$_3$ and a diorganopolysiloxane of formula (II) in the presence of an acid catalyst such as paratoluene sulfonic acid or an earth acid of the Montmorillonite type ("KATALYSATOR KSF/O" sold by S-d-Chemie-A. G. München).

8. Anionic groups of the type:

carboxylic such as the alkylcarboxylic groups as in the product "X-22-3701E" sold by Shin-Etsu, 2-hydroxyalkylsulfonate and 2-hydroxyalkylthiosulfate such as the products sold by Goldschmidt under the trade names "ABIL S201" and ABIL S255".

The volatile silicones are more particularly selected from among:

1. cyclic silicones having 3 to 7 silicon atoms and preferably 4 to 5 silicon atoms such as more particularly octa methylcyclotetrasiloxane sold under the trade name "Volatile Silicone 7207" by Union Carbide or "Silbione 70045 V2" by Rhone Poulenc, or decamethylcyclopentasiloxane sold in particular under the trade name "Volatile Silicone 7158" by Union Carbide or even "Silbione 70045 V 5" sold by Rhone Poulenc, as well as their mixtures.

Mention can also be made of the cyclocopolymers such as dimethylsiloxane/methylalkylsiloxane, and principally the volatile silicone "FZ 3109" sold by Union Carbide, having the structure:

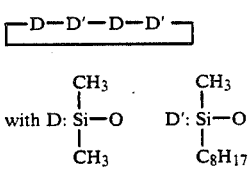

Mention can also be made of mixtures of cyclic silicones with compounds derived from silicon such as the mixture of octamethylcyclotetrasiloxane and tetratrimethylsilyl pentaerythritol (50/50) and the mixture of octamethylcyclotetrasiloxane and oxy-1,1'(hexa-2,2,2',2',3,3' trimethylsilyloxy) bis-neopentane.

2. the linear volatile silicones having 2-9 silicon atoms and possessing a viscosity lower than or equal to $5 \times 10^{-6}$ m$^2$/s at 25° C. Silicones of this type are in particular constituted by hexamethyldisiloxane sold under the trade name "Silbione 70041 V 0.65" by Rhone Poulenc and by decamethyltetrasiloxane sold under the trade name "SH 200" by Toray Silicone. Silicones included in this class are also described in the article published in Cosmetics and Toiletries, Vol. 91, Jan., 1976, p.27-32 and Todd and Byers "Volatile Silicone Fluids for Cosmetics".

The more particularly preferred polyorganosiloxanes, in accordance with the present invention are volatile silicones such as decamethyl cyclopentasiloxane sold under the trade name "Silbione oil 70045V5" by Rhone Poulenc, nonvolatile silicones selected from the family of linear polyalkylsiloxanes having terminal trimethylsilyl groups such as oils having a viscosity between $5 \times 10^{-5}$ and $5 \times 10^{-2}$ m$^2$/s at 25° C., of the 70047 and 47 series and more particularly the 70047V50000 series sold by Rhone Poulenc or the polyalkylarylsiloxanes such as the "ABIL AV 1000" oil sold by Goldschmidt.

The film forming polymers employed in the composition of the present invention can be anionic, cationic, nonionic or amphoteric polymers. These film forming polymers as well as their use in cosmetic compositions for the hair, are known.

Described in more detail below are certain film forming polymers employed in the compositions of the present invention.

The cationic polymers employed in accordance with the present invention are polymers of the polyamine, polyaminopolyamide or polyquaternaryammonium type in which the amine or ammonium group is a part of the polymer chain or is linked to it and they have a molecular weight ranging from 500 to 3,000,000.

The cationic polymers employed in accordance with the present invention are selected principally from among the following polymers:

1. Vinylpyrrolidone-dialkylaminoalkyl acrylate or methacrylate copolymer (quaternized or not) such as those sold under the trade names "GAFQUAT" by the GAF Corporation, as for example, "Copolymer 845", "GAFQUAT 734" or "GAFQUAT 735" described principally in more detail in French patent 2.077.141 and French patent 2.393.573.

2. Cellulose ether derivatives having quaternary ammonium groups such as those described in French patent 1.492.597 and principally the polymers sold under the trade names "JR" such as "JR 125", "JR 400" and "JR 30M", and "LR", such as "LR 400" and "LR 30M" by Union Carbide; the cationic cellulose derivatives such as "CELQUAT L 200" and "CELQUAT H 100" sold by National Starch and described in U.S. Pat. No. 4,131,576.

3. The cationic polysaccharides such as those described in U.S. Pat. Nos. 3,589,978 and 4,031,307 and in particular "JAQUAR C.13" sold by Meyhall.

4. Cationic polymers selected from the group:

(a) polymers containing units of the formula: —A—Z—A—Z— (I) in which A represents a radical having two amine functions and preferably piperazinyl and Z represents B or B', each independently, representing a bivalent radical which is a straight or branched chain alkylene radical having up to 7 consecutive carbon atoms in the principal chain, nonsubstituted or substituted by hydroxy groups and being able to have besides atoms of oxygen, nitrogen, sulfur, 1 to 3 aromatic and/or heterocyclic rings; the atoms of oxygen, nitrogen and sulfur being present in the form of ether or thioether, sulfoxide, sulfone, sulfonium, amine, alkylamine, alkenylamine, benzylamine, amine oxide, quaternary ammonium, amide, imide, alcohol, ester and/or urethane groups; these polymers and the process for their preparation are described in French patent 2.162.025, (b) polymers containing units of the formula: —A—$Z_1$—A—$Z_1$— (II) in which A represents a radical having two amine functions and preferably piperazinyl and $Z_1$ represents $B_1$ or $B'_1$ and it represents at least once $B'_1$; $B_1$ represents a bivalent radical which is a straight or branched chain alkylene or hydroxylakylene radical having up to 7 consecutive carbon atoms in the principal chain, $B'_1$ is a bivalent radical which is a straight or branched chain alkylene having up to 7 consecutive carbon atoms in the principal chain, nonsubstituted or substituted by one or more hydroxyl radicals and interrupted by one or more nitrogen atoms, the nitrogen atom being substituted by an alkyl chain optionally interrupted by an oxygen atom and optionally having one or more hydroxyl functions; these polymers and the process for their preparation are described in French patent 2.280.361.

(c) alkylation products with alkyl or benzyl halides, lower alkyl tosylates or mesylates and the oxidation products of the polymers of formulas (I) and (II) indicated above in (a) and (b).

5. cyclopolymers having a molecular weight ranging from 20,000 to 3,000,000 such as homopolymers having as the principal constituent in the chain, units having formula (III) or (III'):

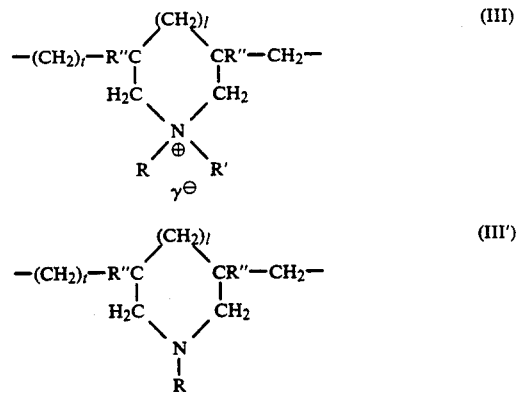

wherein l and t are equal to 0 or 1 and the sum l+t=1,

R" represents hydrogen or methyl,

R and R", each independently represent alkyl having 1-22 carbon atoms, hydroxyalkyl in which the alkyl moiety has preferably 1-5 carbon atoms, lower amidoalkyl and where R and R' can together with the nitrogen atom to which they are attached represent heterocyclic groups such as piperidinyl or morpholinyl, as well as copolymers containing units of formula III or III' and units derived from acrylamide or diacetone acrylamide, $\gamma^\ominus$ is an anion such as bromide, chloride, acetate, borate, citrate, tartrate, bisulfate, bisulfite, sulfate or phosphate.

Among the quaternary ammonium polymers of the type defined above, mention can be made of the homopolymer of dimethyl diallyl ammonium chloride sold under the trade name "MERQUAT 100" having a molecular weight lower than 100,000 and the copolymer of dimethyl diallyl ammonium chloride and acrylamide having a molecular weight greater than 500,000 and sold under the trade name "MERQUAT 550" by Merck.

These polymers are described in French patent 2.080.759 and its certificate of addition No. 2.190.406.

The anionic polymers are polymers having a molecular weight ranging from 500 to 3,000,000 and having carboxylic and/or sulfonic groups.

The carboxylic groups are brought into the anionic polymers by unsaturated carboxylic mono or diacids represented principally by the formula

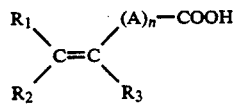

wherein n is a number ranging from 0 to 10,

A represents a methylene group optionally linked to the carbon atom of the unsaturated group or to the neighboring methylene group when n is greater than 1 by the intermediate of a heteroatom such as oxygen or sulfur, $R_1$ represents hydrogen, phenyl or benzyl, $R_2$ represents hydrogen, lower alkyl or carboxyl, $R_3$ represents hydrogen, lower alkyl, —$CH_2$—COOH, phenyl or benzyl.

In the foregoing formula a lower alkyl radical represents preferably a group having 1-4 carbon atoms and in particular methyl and ethyl.

The preferred anionic polymers employed in accordance with the present invention are selected principally from among:

homo- or copolymers of acrylic or methacrylic acids or their salts and in particular the products sold under the trade names "VERSICOL F" or "VERSICOL K", by Allied Colloid, "ULTRAHOLD 8" by Ciba Geigy, the copolymers of acrylic acid and acrylamide sold under the form of their sodium salt under the trade names "RETEN 421, 423 or 425" by Hercules, sodium polymethacrylate sold under the trade name "DARVAN No. 7" by Van der Bilt, the sodium salts of polyhydroxycarboxylic acids sold under the trade name "HYDAGEN X" by Henkel;

the copolymers derived from crotonic acid such as those having in their chain vinyl acetate or propionate units and optionally other monomers such as allylic or methallylic esters, vinyl ether, or vinyl ester of a long chain hydrocarbon saturated carboxylic acid such as those having at least 5 carbon atoms or even a vinyl, allyl or methallyl ester of a carboxylic or cyclic acid, these polymers being able optionally to be grafted and crosslinked. Such polymers are described, among others, in French patents 1.222.944, 1.580.545, 2.265.782, 2.265.781, 1.564.110 and 2.439.798. Commercial products of this class of polymers are the resins "28-29-30", "26-13-14" and "28-13-10" sold by National Starch;

copolymers of acrylic or methacrylic acids with esters of acrylic or methacrylic acids;

copolymers of crotonic acid and vinyl esters grafted on a polyalkyleneglycol such as polyethyleneglycol such as the crotonic acid/vinyl acetate copolymer grafted on polyethyleneglycol sold under the trade name "ARISTOFLEX A" by Hoechst.

The polymers derived from maleic, fumaric, and itaconic acids or anhydrides with vinyl esters, vinyl ethers, vinyl halides, phenylvinyl derivatives, acrylic acid and its esters; these polymers can be esterified. Such polymers are described in particular in EUA patents 2.047.398, 2.723.288, 2.102.113, and British patent 839.805.

Mention can principally be made of the polymers sold under the trade name "GANTREZ AN, S or ES" by General Anilin or "EMA 1325 or 9" by Monsanto. Polymers also belonging in this class are copolymers of maleic, citraconic and itaconic anhydride and an allylic or methallylic ester having optionally an acrylamide or methacrylamide group in their chain, monoetsterified or monoamidofied, described in French patents 2 350 834 and 2.357.241.

The polymers having a sulfonic group employed in accordance with the present invention are selected principally from among:

salts of polystyrene sulfonic acid such as the sodium salts sold under the trade name "FLEXAN 500" having a molecular weight of about 500,000 or under the trade name "FLEXAN 130" having a molecular weight of about 100,000 by National Starch. Such compounds are described principally in French patent 2.198.719;

salts of sulfonic polyacrylamide, such as those mentioned in U.S. Pat. No. 4,128,631 and more particularly polyacrylamidoethylpropane sulfonic acid sold under the trade name "COSMEDIA POLYMER HSP 1180" by Henkel.

The amphoteric film forming polymers employed in accordance with the present invention are polymers having A and B units statistically distributed in the polymer chain where A represents a unit derived from a monomer having at least one basic nitrogen atom and B represents a unit derived from an acid monomer having one or more carboxylic or sulfonic groups or indeed A and B being able to represent groups derived from carboxybetain zwitterionic monomers;

A and B can also represent a cationic polymer chain having secondary, tertiary or quaternary amine groups, in which at least one of the amine groups carries a carboxylic or sulfonic group linked by the intermediate of a hydrocarbon radical or indeed A and B are part of a chain of a polymer having an $\alpha,\beta$-dicarboxylic ethylene unit of which one of the carboxylic groups has been reacted with a polyamine having one or more primary or secondary amine groups.

The more particularly preferred amphoteric polymers responding to the definition given above are selected from among the following polymers:

(1) polymers having units derived from (a) at least one monomer selected from acrylamides or methacrylamides substituted at the nitrogen by an alkyl radical, (b) at least one acid comonomer containing one or more reactive carboxylic groups, and (c) at least one basic comonomer such as esters having primary, secondary, tertiary and quaternary amine substituents of acrylic and methacrylic acids and the quaternization product of dimethylaminoethyl methacrylate with dimethyl or diethyl sulfate.

The more particularly preferred N-substituted acrylamides or methacrylamides according to the present invention are groups whose alkyl radicals contain from 2 to 12 carbon atoms and more particularly N-ethylacrylamide, N-tert. butylacrylamide, N-tert.octyl acrylamide, N-octylacrylamide, N-decylacrylamide, N-dodecylacrylamide as well as the corresponding methacrylamides. The acid comonomers are more particularly selected from among acrylic, methacrylic, crotonic, itaconic, maleic and fumaric acids as well as the alkyl monoesters having 1-4 carbon atoms of maleic acid or fumaric acid.

The preferred basic comonomers are aminoethyl methacrylate, butylaminoethyl methacry late, N,N'-dimethylaminoethyl methacrylate and N-tert. butylaminoethyl methacrylate.

As compounds representative of this class mention can be made of "AMPHOMER" which is an N-tert. octyl acrylamide/methyl methacrylate/hydroxypropyl methacrylate/acrylic acid/tert. butyl aminoethyl methacrylate copolymer sold by National Starch.

(2) polymers derived from chitosan having monomer units having the following formulas:

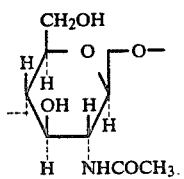

-continued (B) 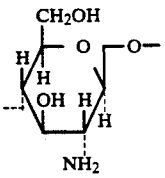

(C) 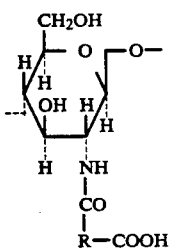

in which the unit A is present in amounts ranging from 0 to 30%, B is present in amounts ranging from 5 to 50% and C is present in amounts ranging from 30 to 90%. In formula C, R represents a radical of the formula

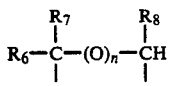

wherein if n=0, $R_6$, $R_7$ and $R_8$, each independently represent hydrogen, methyl, hydroxyl, acetoxy, amino, monoalkylamino or dialkylamino optionally interrupted by one or more nitrogen atoms and/or optionally substituted by one or more groups selected from amine, hydroxyl, carboxyl, alkylthio, sulfonic, alkylthio whose alkyl moiety carries an amino group, with at least one of the $R_6$, $R_7$ and $R_8$ radicals being in this case hydrogen; or n is equal to 1, in which case $R_6$, $R_7$ and $R_8$ each represent hydrogen, as well as the salts formed by these compounds with bases or acids.

The polymers derived from chitosan employed in the compositions according to the present invention can be prepared by acylation of chitosan with an acid anhydride conforming to the operating method described in Example 1 of French patent No. 2.137.684 or in U.S. Pat. No. 3,879,376. A polymer derived from chitosan, more particularly preferred in accordance with the present invention has 0-20% by weight of A units, 40 to 50% by weight of B units and 40 to 50% by weight of C units, this latter unit having the formula ($C_1$) 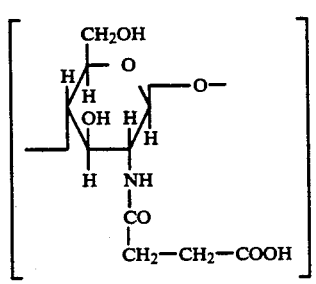

This preferred polymer constituted of A, B and $C_1$ units will be denominated by the following: polymer ($P_1$).

(3) amphoteric polymers of the —A—Z—A—Z— type selected from (a) polymers obtained by the action of chloracetic acid or sodium chloracetate on compounds containing at least one unit of the formula $$—A—Z—A—Z—A—\qquad (V)$$

wherein

A represents

and

Z represents B or B', each independently, representing a bivalent radical which is a straight or branched chain alkylene having up to 7 carbon atoms in the principal chain, nonsubstituted or substituted by hydroxyl groups and being able to have besides atoms of oxygen, nitrogen and sulfur, 1-3 aromatic and/or heterocyclic rings; the atoms of oxygen, nitrogen and sulfur being present in the form of ether, thioether, sulfoxide, sulfone, sulfonium, alkylamine, alkenylamine, hydroxyl, benzylamine, amine oxide, quaternary ammonium, amide, imide, alcohol, ester and/or urethane groups.

(b) polymers obtained by the action of chloracetic acid or sodium chloracetate on compounds of the formula $$—A—Z—A—Z—\qquad (V)$$

wherein

A represents

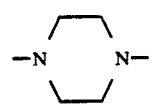

and

Z represents B or B' and at least one B';

B having the meaning indicated above and

B' is a bivalent radical which is a straight or branched chain alkylene having up to 7 carbon atoms in the principal chain, substituted or not by one or more hydroxyl radicals and having one or more atoms of nitrogen, the nitrogen atom being substituted by an alkyl chain optionally interrupted by an oxygen atom and necessarily having one or more hydroxyl and/or carboxyl functions, as well as the quaternary ammonium salts resulting from the reaction of chloracetic acid or sodium chloracetate on the polymers of formula (V).

(4) the sulfonic keratins are keratins having a molecular weight between 10,000 and 100,000, obtained starting with goose or chicken feathers or more advantageously with horse hooves or horn.

This keratin is obtained by oxidation of all or part of the disulfide bonds of the cystine groups of the keratin into cysteic acid groups, this oxidation being followed or not by a salification of the $SO_3H$-acid groups, the oxidation being advantageously carried out in an acid medium such as formic acid, using an oxidizing agent such as $H_2O_2$.

(5) copolymers or diallyl (C₁-C₄) dialkyl ammonium chloride/acrylic acid such as the product sold under the trade name "MERQUAT 280" by Merck which is a copolymer of diallyl dimethyl ammonium chloride/acrylic acid.

The nonionic polymers employed in accordance with the present invention are principally:

polyvinylpyrrolidone or copolymers of vinylpyrrolidone with nonionic comonomers such as the polyvinylpyrrolidone/vinyl acetate copolymer sold under the trade name "PVP/VA S 630" by GAF, nonionic vinyl homopolymers or copolymers such as polyvinyl alcohol sold under the trade name "MOWIOL 4088" by Hoechst, poly-β-alanines described more particularly in Belgian patent No. 208,516.

These polymers have from 50 to 100% of repeating units having the formula

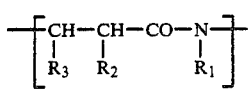
(I)

and 0 to 50% of repeating units of the polyacrylamide type having the following formula:

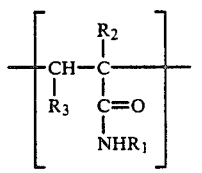
(II)

wherein

R₁ represents hydrogen or a radical selected from the group consisting of (i)

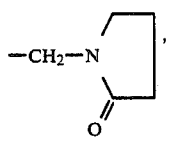

(ii) —CH₂OH, (iii) —(CH₂)$_{n'}$—CH₃ wherein n' is 0 or a number ranging from 1 to 11, and (iv) —(CH₂—CH₂—O)$_m$—H wherein m is a number ranging from 1 to 10, and R₂ and R₃ represent hydrogen or methyl.

These polymers are prepared more particularly by the polymerization of acrylamide, as described in U.S. Pat. No. 4,082,730. These polymers preferably have a molecular weight between 500 and 100,000 and more particularly between 2,000 and 60,000.

The derivatives of polyaspartic acid such as those described in French patent No. 77.27769 (publication No. 2.403.076). The said polyaspartic acid derivatives have the formula III:

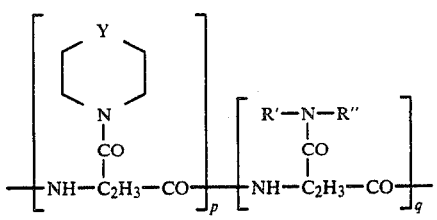

wherein

R' represents hydrogen, lower hydroxyalkyl, lower hydroxyalkyloxyalkyl, alkyl having more than 18 carbon atoms or alkenyl having 2-18 carbon atoms, R" represents hydrogen, lower hydroxyalkyl or lower alkyl, Y represents methylene, —O—, N(R''') or

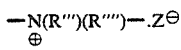

wherein

R''' and R'''' represent hydrogen, C₁-C₁₈ alkyl, C₂-C₁₈ alkenyl and Z⊖ is an anion.

The particularly preferred film forming polymers are:

for cationic polymers:

vinylpyrrolidone/diaminoalkyl acrylate or methacrylate copolymers of group 1 such as the product sold under the trade name "GAFQUAT 734" by GAF, cationic cellulose ether derivatives and cationic cellulose derivatives of group 2 and principally products sold under the trade name "JR 400" and CELQUAT LOR", cyclopolymers of group 9 and principally the product sold under the trade name "MERQUAT 550";

for the anionic polymers:

polymers derived from maleic acid or anhydride, such as the polymer sold under the trade name "GANTREZ ES 425";

for the amphoteric polymers:

polymers derived from chitosan of group 2 such as the polymer (P₁) named above and sulfonic keratins;

for the nonionic polymers;

vinylpyrrolidone/vinylacetate copolymer such as the product sold under the trade name "PVP/VA S 630" sold by GAF.

The film forming polymers are present, in the compositions of the invention, in a weight amount at least equal to 0.1 percent and lower than 2%, and in particular between 0.1 and 1 weight percent.

Preferably, the weight ratio, film forming polymer/silicone is greater than 0.25 and lower than 8, and in particular greater than 0.5 and lower than 6.

The cosmetic compositions of the present invention can also contain one or more conventional secondary ingredients such as thickening agents, stabilizing agents, perfumes or preservatives.

Compositions without a thickening agent are fluid lotions. Compositions with a thickening agent are lotions or fluid gels.

The thickening agents are more particularly selected from among polyacrylic acids crosslinked by a polyfunctional agent such as the products sold under the trade name "CARBOPOL" by Goodrich, such as the "CARBOPOLS" 910, 934, 934P, 940, 941 and 1342, or cellulosic derivatives such as hydroxymethylcellulose, carboxymethylcellulose, hydroxybutylcellulose, hydroxypropylcellulose, and more particularly, hydroxyethylcellulose, such as the products sold under the trade name "NATROSOL" (150,250) by Hercules or "CELLOSIZE" (QP and WP) by Union Carbide, methylhydroxypropylcellulose, in particular the products sold under the trade name "METHOCEL" (E, F, J and K) by Dow Chemical or the heterobio-polysaccharides such as for example xanthan gums sold under the mark "KELTROL" and "KELZAN" by Kelco, "RHODOPOL" and "RHODIGEL" by Rhone Poulenc, or "ACTIGUM" by Ceca/Satia.

When thickening agents are employed, they are preferably selected from among the "CARBOPOLS" and are employed preferably in a concentration such that the viscosity of the composition is at most equal to about 25 poises (2.5 Pa.s) at 25° C. (Contraves viscosimeter: measurement body No. 3; rotation time - 10 minutes, at 200 rpm).

As stabilizing agents, mention can be made of the phosphoric esters of fatty alcohols. They are generally employed at a concentration lower than 1 percent.

The preservatives are, for example, parahydroxybenzoic acid, its salts and esters, sorbic acid and its salts, dimethyloldimethylhydantoin and derivatives of imidazolidinyl urea. They are employed at conventional efficacious concentrations.

The pH of the compositions obtained in accordance with the present invention can vary from 3 to 10. The pH optionally can be adjusted using a conventional pH modifying agent.

The compositions according to the present invention are obtained by the hot formation of a microemulsion. More precisely, these compositions are obtained by a process principally characterized by the fact that the wax and the emulsifying agent are heated to a temperature greater than the melting temperature of the wax and not greater than 100° C., optionally in the presence of a portion of water, until complete melting of the wax. Water, or the remainder of the water, is progressively added and the mixture is heated to a temperature at least equal to the said temperature, by stirring, up to the formation of a wax microemulsion in the continuous aqueous phase. The whole is then cooled to ambient temperature. A stable wax microdispersion is thus obtained.

The liposoluble ingredients, for example ceramides, are generally added to the wax, before producing the microdispersion.

The hydrosoluble ingredients can be added in the water employed to produce the microdispersion, or in the finally obtained wax microdispersion.

Also, the secondary ingredients optionally present in the composition are added according to the situation either in the starting products or in the final product.

In accordance with a particular embodiment, the film forming polymer and the silicone are added, with stirring, after producing the wax microdispersion.

The compositions of the present invention are dilutable with water without harming the stability of the microdispersion. They can then be provided in the form of concentrated compositions whose amount of ingredients can be adjusted to a desired value by the simple addition of water.

The compositions of the present invention can be applied on dry or wet hair, clean or not. They can be rinsed or not rinsed.

Notwithstanding the presence of a wax in the composition, no oily appearance is imparted to the hair, even in the absence of rinsing. Moreover, notwithstanding the presence of a high amount of water in the composition, drying poses no problems and is effected rapidly.

The present invention also relates to a process for the cosmetic treatment of hair and/or the scalp, characterized by the fact that there is applied to the hair an effective amount of the composition defined above.

The frequency of application can vary, for example, between a daily application to a weekly application.

The following non-limiting examples illustrate the present invention.

The commercial names employed in the examples represent the following products:

"GANTREZ ES 425": methylvinylether/maleic anhydride monoesterified with butanol at 50% active material in ethanol, sold by GAF;

"MOWIOL 48-88": polyvinyl alcohol sold by Goodrich;

"PVP/VA S 630": vinylpyrrolidone/vinylacetate copolymer (60/40) sold by GAF;

"CELQUAT LOR": hydroxyethylcellulose/diallyldimethyl ammonium chloride copolymer, sold by National Starch;

"GAFQUAT 734": polyvinylpyrrolidone/dimethylaminoethyl methacrylate copolymer quaternized by diethyl sulfate having a molecular weight of 100,000 and sold by GAF, 50% active material in ethanol;

"FLUID DC 200 (12500 Cst)": polydimethylsiloxane oil (viscosity - 12500 Cst at 25° C.) sold by Dow Corning;

"ABIL AV 1000": polymethylphenylsiloxane oil (viscosity - 1000 Cst at 25° C.) sold by Goldschmidt;

"SILBIONE 70047V5000": polydimethylsiloxane oil (viscosity - 5000 Cst at 25° C.) sold by Rhone Poulenc; and "SILBIONE 70045V5": decamethylcyclopentasiloxane, sold by Rhone Poulenc.

EXAMPLES 1-10

The following compositions are prepared (weight amounts in grams of active material):

| Silicones | EXAMPLES | | | | | | | | | |
|---|---|---|---|---|---|---|---|---|---|---|
| | 1 | 2 | 3 | 4 | 5 | 6 | 7 | 8 | 9 | 10 |
| "Silbione 70047V5000" (R.P.) | 0.05 | | | | 0.05 | 0.05 | 0.05 | 0.05 | | |
| "Silbione 70045V5" (R.P.) | | 0.05 | | | | | | | 0.05 | |
| "Fluid DC200" (12500 Cst)(D.C.) | | | 0.05 | | | | | | | |
| "PPMS ABIL AV 1000" (Goldschmidt) | | | | 0.05 | | | | | | 0.05 |
| "PA" | | | | | | | | | | |
| "Gantrez ES 425" (GAF) | 0.2 | | | | | | | | 0.2 | 0.2 |
| PC | | | | | | | | | | |
| "CELQUAT LOR" N.S. | | 0.2 | | | | | | | | |
| "GAFQUAT 734" 50% MA (GAF) | | | | | 0.2 | | | | | |
| PNI | | | | | | | | | | |
| "PVP/VA S 630 (GAF) | | | | | | | 0.2 | | | |

-continued

| Silicones | 1 | 2 | 3 | 4 | 5 | 6 | 7 | 8 | 9 | 10 |
|---|---|---|---|---|---|---|---|---|---|---|
| "MOWIOL 40-88" (HOECHST) PAM |  |  | 0.2 |  |  |  |  |  |  |  |
| Derivative chitosane "P1" |  |  |  | 0.2 |  |  | 0.2 |  |  |  |
| Keratin sulfonic |  |  |  |  |  |  |  | 0.2 |  |  |
| Composition A | 90 | 90 | 90 | 90 | 90 | 90 | 90 | 90 | 90 | 90 |
| Sodiumhydroxide | 0.035 |  |  |  |  |  |  |  | 0.035 | 0.035 |
| Lactic acid |  |  |  | 0.19 |  |  | 0.19 |  |  |  |
| Water, sufficient amount for | 100 | 100 | 100 | 100 | 100 | 100 | 100 | 100 | 100 | 100 |

This preparation is effected by adding the requisite amount of film forming polymer and silicone to the microdispersion of composition A, which has the weight indicated below. Finally, the case occurring, lactic acid or sodium hydroxide is added.

| Composition A: | |
|---|---|
| Autoemulsifiable wax, sold under the trade name "CIRE AUTOLUSTRANTE OFR" by Tisco | 12 g |
| Triethanolamine, sufficient for pH = 5 | |
| Preservatives, sufficient amount | |
| Water, sufficient amount for | 100 g |

The "OFR" wax is heated to 90°–95° C. with stirring. There is then progressively added, with reduced stirring, 70 percent of the total amount of water heated to 90° C. and including a preservative. The mixture is permitted to return to 30° C. with mild stirring, and the pH is adjusted with triethanolamine. Preservatives are then added as well as the remaining water to make 100 g.

EXAMPLE 11

In an analogous manner, the following composition is prepared:

| | |
|---|---|
| Composition B | 18 g |
| "71615V300RP" oil (polydimethylsiloxane having hydroxypropylated group, MW, 9000) | 0.5 g |
| Hydroxyethylcellulose crosslinked with epichlorohydrin and quaternized with triethanolamine, sold by GAF under the trade name "JR 400" | 0.3 g |
| Sorbitan monolaurate, polyoxyethylenated with 20 moles of ethylene oxide | 3.0 g |
| Hydroxyethylcellulose | 1.0 g |
| Water, sufficient amount for | 100 g |
| The pH is adjusted to 4 with lactic acid. | |
| Composition B has the following contents: | |
| Carnauba wax | 30 g |
| Glycerol monostearate polyoxyethylenated with 30 moles of ethylene oxide, sold by Goldschmidt under the trade name "TAGAT S" | 7.5 g |
| Preservative | 0.2 g |
| Water, sufficient amount for | 100 g |

Tests on Hair

These test have been effected with the compositions of Examples 1–10 as well as with analogous compositions lacking either the film forming polymer or the silicone. The results are compared to those obtained with the "blank microdispersion" (without film forming polymer or silicone) which serves as the control.

The procedures employed are indicated below.

SOFTNESS TEST

Operation 0.25 g of the composition being studied is spread on 5 g samples of natural hair. The hair samples are combed and dried under a hood for 15 minutes. The hair samples are cooled and their softness is evaluated.

Evaluation

The softness of the sample under consideration is evaluated by comparative touching with respect to the control sample.

A given sample is employed at most for only two evaluations, thus avoiding problems of a modification of the softness induced by successive manipulations of the samples.

The test is carried out on a panel composed of 5 testers at a minimum.

TEST OF LIVELINESS

Operation 0.25 g of the composition be.ng studied is spread on a 2.5 g hair sample having a length of 25 cm. The sample is combed and rolled up on a roller of 2 cm in diameter (number of windings=4). The sample, mounted on the roller, is dried in a hood for 15 minutes. The sample is cooled before unrolling it and installing it in the apparatus described below which permits to evaluate its liveliness.

Apparatus

There is employed, for this evaluation, an apparatus which imposes on the samples, fixed by their two extremities to the said apparatus, known alternating vertical movement of course and speed under the following reproducible operating compositions: 100 cycles at a rate of 50 cycles/min.

At the end of these constraints, the lower extremity of the sample is freed and a visual and touch evaluation of its liveliness is carried out.

Each composition is evaluated by 5 or 6 testers.

The visual examination permits to select the samples still curled and not relaxed which are then submitted to a touch evaluation consisting in evaluating by touch "the spring effect" of the curled samples.

Results

The compositions according to the present invention have been judged to be superior in softness and liveliness compared to the "blank microdispersions" (without film forming polymer and silicone) by at least 80% of the testers. The compositions of Examples 1–4 were judged superior by 100% of the testers.

We claim:

1. A cosmetic composition for the hair comprising at least one film forming polymer present in an amount ranging from 0.1 to 2 weight percent and at least one silicone present in an amount ranging from 0.01 to 1 weight percent incorporated into a support consisting essentially of a wax microdispersion in an aqueous liquid vehicle of which the dispersed phase is a stable microdispersion of particles having a size lower than 500 nm, the said particles consisting essentially of a wax or mixture of waxes, the said wax or mixtures of waxes having a final melting point greater than 60° C. and lower than 100° C. and being capable of forming a microdispersion as defined above, the said composition containing, by weight, from 0.1 to 40 percent of wax and at least one emulsifying agent present in an amount ranging from 0.01 to 25 weight percent and wherein the wax/emulsifying agent weight ratio is in the range of 1 to 20 and wherein the film forming polymer/silicone weight ratio is greater than 0.25 and lower than 8.

2. The composition of claim 1 wherein at least 50 weight percent of said wax is selected from Carnauba wax, Candelilla wax, Alfa wax and mixtures thereof.

3. The composition of claim 1 wherein said wax is selected from Carnauba wax, Candelilla wax, Alfa wax and mixtures thereof.

4. The composition of claim 1 wherein said wax is present in an amount ranging from 1 to 20 weight percent.

5. The composition of claim 1 wherein said wax is present in an amount ranging from 1 to 15 weight percent.

6. The composition of claim 1 wherein said wax is present in an amount ranging from 1 to 10 weight percent.

7. The composition of claim 1 wherein said emulsifying agent is an anionic or nonionic surfactant.

8. The composition of claim 1 wherein said emulsifying agent is present in a amount ranging from 0.1 to 10 weight percent.

9. The composition of claim 1 wherein the wax/emulsifying agent weight ratio is in the range of 2 to 10.

10. The composition of claim 1 wherein said silicone is present in an amount ranging from 0.02 to 0.5 weight percent.

11. The composition of claim 1 wherein said film forming polymer is present in an amount ranging from 0.1 to 1 weight percent.

12. The composition of claim 1 wherein the film forming polymer/silicone weight ratio is greater than 0.5 and lower than 6.

13. A process for the cosmetic treatment of hair comprising applying to said hair an effective amount of the composition of claim 1.

* * * * *